US009392983B2

(12) United States Patent
Linev

(10) Patent No.: US 9,392,983 B2
(45) Date of Patent: *Jul. 19, 2016

(54) MULTI-BEAM STEREOSCOPIC X-RAY BODY SCANNER

(71) Applicant: ADANI Systems, Inc., Alexandria, VA (US)

(72) Inventor: Vladimir N. Linev, Minsk (BY)

(73) Assignee: ADANI SYSTEMS, INC., Alexandria, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/014,237

(22) Filed: Feb. 3, 2016

(65) Prior Publication Data

US 2016/0143601 A1    May 26, 2016

Related U.S. Application Data

(63) Continuation of application No. 14/463,748, filed on Aug. 20, 2014, now Pat. No. 9,277,897.

(51) Int. Cl.
*G01N 23/04* (2006.01)
*A61B 6/00* (2006.01)
*A61B 6/06* (2006.01)
*A61B 6/04* (2006.01)

(52) U.S. Cl.
CPC ............ *A61B 6/4014* (2013.01); *A61B 6/04* (2013.01); *A61B 6/06* (2013.01); *A61B 6/4078* (2013.01); *A61B 6/4405* (2013.01)

(58) Field of Classification Search
CPC ........................ G01V 5/0008; G01V 5/0033
See application file for complete search history.

(56) References Cited

U.S. PATENT DOCUMENTS

| | | | | |
|---|---|---|---|---|
| 5,065,418 A * | 11/1991 | Bermbach | ............ | G01V 5/0016 250/358.1 |
| 6,094,472 A * | 7/2000 | Smith | ................. | G01N 23/203 378/86 |
| 9,277,897 B1 * | 3/2016 | Linev | ................... | A61B 6/4405 |

* cited by examiner

*Primary Examiner* — Hoon Song
(74) *Attorney, Agent, or Firm* — Bardmesser Law Group

(57) ABSTRACT

An X-ray examination station includes a first source of X-ray radiation for whole body scanning of a human body using a first fan beam of X-ray radiation; a first vertical linear radiation detector configured to detect the first fan beam; a second source of X-ray radiation installed at mid-height of a person being examined, for scanning a central portion of the human body using a second fan beam of X-ray radiation; a second vertical detector of X-ray radiation configured to detect the second fan beam; and a control unit configured to turn on each of the X-ray radiation sources. The first and the second radiation fan beams are emitted in parallel planes. The first X-ray radiation source is turned on for the whole body scanning. The second X-ray radiation source is turned on for scanning the central portion of the body.

19 Claims, 16 Drawing Sheets

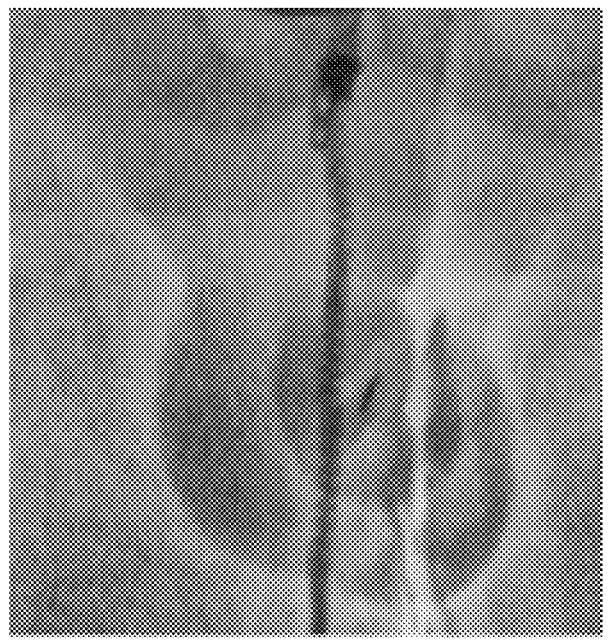
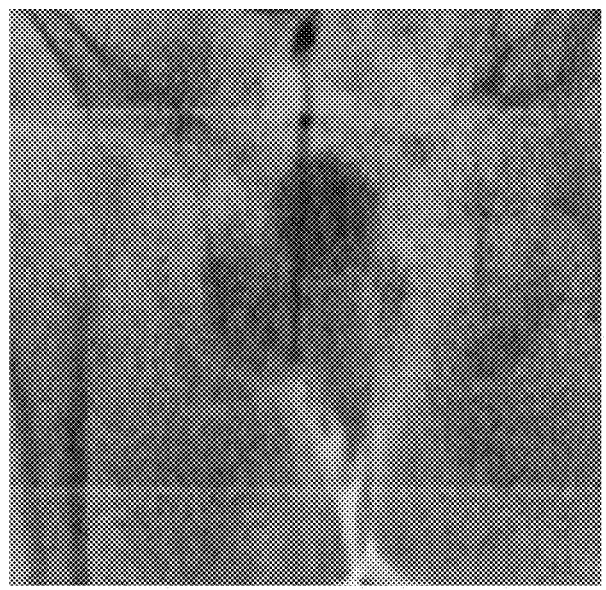
FIG. 8

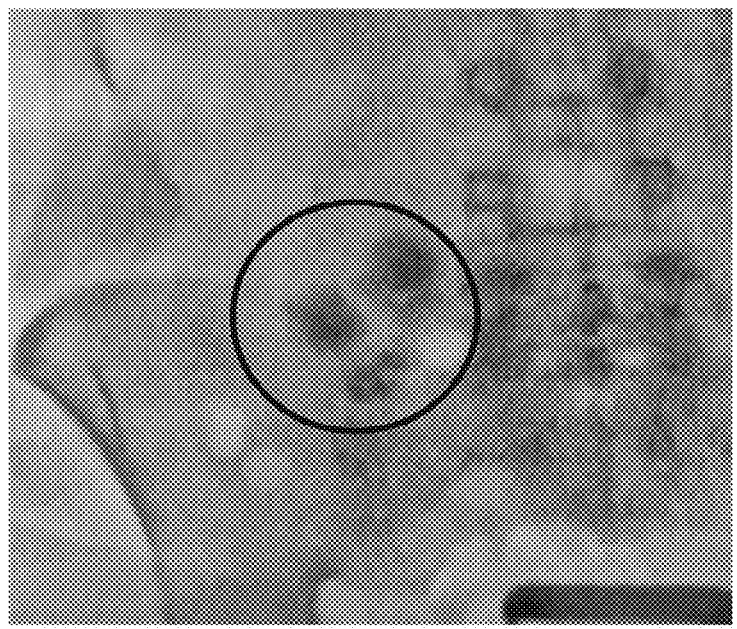
PACKAGES WITH DRUGS – DUAL VIEW SYSTEM IMAGE
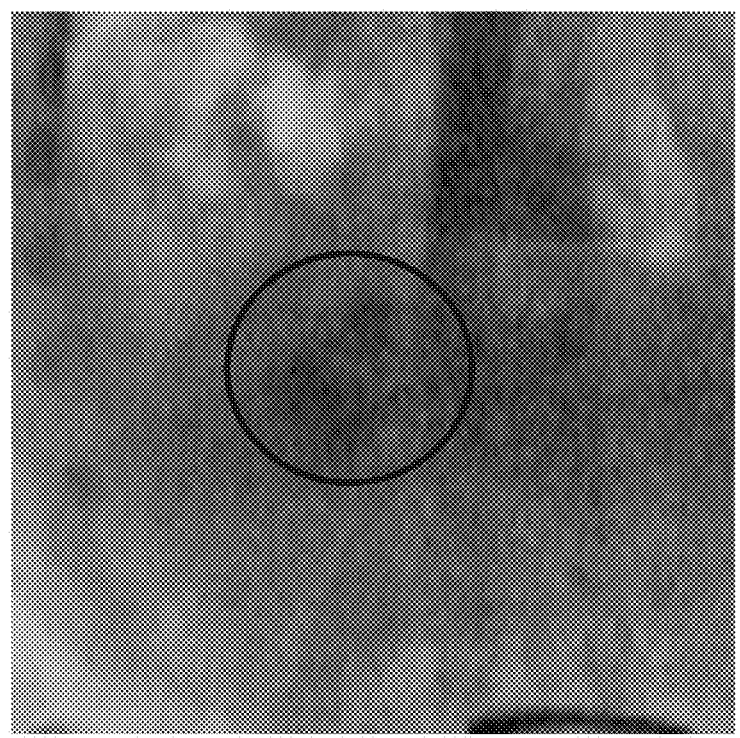
PACKAGES WITH DRUGS – SINGLE VIEW SYSTEM IMAGE
FIG. 11

MULTI-BEAM STEREOSCOPIC X-RAY BODY SCANNER

CROSS REFERENCE TO RELATED APPLICATIONS

This application is a continuation of U.S. patent application Ser. No. 14/463,748, filed on Aug. 20, 2014, incorporated herein by reference in its entirety.

BACKGROUND OF THE INVENTION

1. Field of the Invention

The invention relates to the field of engineering physics, and, in particular, to X-ray scanning for harmful objects or substances located on a human body or hidden in body cavities in order to prevent theft or terrorist acts in buildings, airports, malls, train station, subways and other public places.

2. Description of the Related Art

Human body X-ray scanning for identifying some highly undesirable objects or substances has become critically important in view of terrorist threats. Security applications may include prevention of smuggling of drugs, precious stones and metals, as well as provision of the security at airports, banks, embassies, nuclear power centers and other high-risk locations. X-ray luggage examination in airports is currently the most efficient way to provide the security of the flights. X-ray examination is also used in prisons for visitor's access control.

X-ray luggage examination systems are designed as a conveyer passing through a rectangular frame with an X-ray source installed in the upper part of the frame and a detector of X-radiation installed in the lower part of the frame under the conveyor. However, the described system is not designed for scanning of the passengers due to high level of radiation emitted by an X-ray source, which is used to increase the resolution of the images.

Scanning of passengers for presence of metallic objects hidden under clothing is provided with the help of electromagnetic frames and metal detectors. An X-ray method has not been used until recently for the examination due to its harmful effects on people, especially in cases of frequent use. A number of efforts have been attempted lately to use a low-dose X-ray scanning, which could be applied to examination of people without any threat to their health. One of these systems is X-ray scanning apparatus named Body Search produces by American Science and Engineering, Inc.

A person is scanned with a beam of X-radiation of sufficiently low intensity, while the radiation transmitted through the person's body is converted into an image, which is used to determine the presence of concealed objects. The Body Search system includes housing with an X-ray source of low-intensity, means for shaping an X-ray beam and a detector of X-radiation transmitted through the clothing and reflected by the body. The reflected X-radiation is detected by the detector to generate an image of the objects located on the surface of the body, in the clothing or on the clothing of the portion of the body turned towards the housing with X-ray source.

For full examination it is necessary to make scanning in two positions—i.e., the face towards the housing and the back towards the housing. With this method the internal cavities of the body that are very often used for concealment of drugs and precious stones are not subjected to the examination. Besides, the strongest radiation effects the most sensitive human organs located in the medium portion of the body, while the person's feet and especially shoes that may be used for concealing the contraband are out of the view of the examiner.

Conventional stationary examinations stations employ a single source of low-intensity X-ray radiation. An integrated collimator and a detector of X-ray radiation passed through the body of the person being examined are used. The system also includes a data processing module and a platform for supporting the person being examined. The disadvantage of this system is its stationary nature—it is hard to relocate and calibrate this scanner. Also, such scanners show poor performance for many objects hidden inside body cavities, depending on the angle of orientation of the object and the X-ray beam.

The mobility issue is addressed by an X-ray scanner located in the back of a truck (see EP2458408). An operator workplace and an X-ray scanner system are located in the back of the truck. The system includes a source of X-ray radiation with at least one slit collimator located approximately at a person's navel level. The system also includes a linear detector of X-ray radiation that has passed through the body of the person being examined. The X-ray compartment has two vertical columns with a platform that moves laterally between the columns.

However, the most sensitive body organs located in the middle portion of the body are exposed to the radiation, while legs and, especially, shoes (often used for smuggling objects) are not fully examined by the scanner. Furthermore, the system cannot scan the person's body in a single cycle. Several scans are needed, which reduces the efficiency of the system, because the person has to step onto the platform and remain still during the scan.

Accordingly, there is a need in the art for a safe mobile X-ray scanner system that provides for a complete X-ray scan of person with a high accuracy and improved efficiency.

SUMMARY OF THE INVENTION

Accordingly, the present invention is related to a high-efficiency multi-beam stereoscopic X-ray scanner that substantially obviates one or more of the disadvantages of the related art.

In one aspect of the invention, a module for processing and visualization of digital signals and an X-ray module are located in a back of a van. The digital X-ray module includes two sources of low-intensity X-ray radiation with at least one slit collimator and a linear detector of X-ray radiation passing through the body of the person being examined. The X-ray module has two vertical columns and a mobile platform located between these columns for supporting and moving the person being examined. (As an alternative, a conveyor-belt type transporter can be used.)

The columns are located along the vertical axis of the body of the van, while the platform moves in a horizontal plane across the body of the van between the columns. The detector of the X-ray radiation is located along the entire length of one of the columns. The slit collimator is integrated in the second column. The collimator is rigidly connected to the source of radiation located on a special platform located near the outer surface of the second column.

The source of the radiation is located on a special platform and can move along a vertical axis. The second column has rails for vertical movement of the slit collimator. The platform with the source of the radiation at its most low position creates a horizontal plane passing through the bottom of the person's body dissects a pre-set number of degrees from the radiation rays. The radiation source platform can be moved in a vertical plane by a hydraulic lift.

Additional features and advantages of the invention will be set forth in the description that follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE ATTACHED FIGURES

The accompanying drawings, which are included to provide a further understanding of the invention and are incorporated in and constitute a part of this specification, illustrate embodiments of the invention and together with the description serve to explain the principles of the invention.

In the drawings:

FIGS. 6-11 illustrate exemplary images produced by the X-ray system.

DETAILED DESCRIPTION OF THE PREFERRED EMBODIMENTS

Reference will now be made in detail to the preferred embodiments of the present invention, examples of which are illustrated in the accompanying drawings.

In one aspect of the invention, a module for processing and visualization of digital signals and one or more X-ray modules are either stationary or located in a back of a van or a truck. The digital X-ray module includes two sources of X-ray radiation. Each of the X-ray sources has one slit collimator to produce a fan beam, and one a linear detector of X-ray radiation passing through the body of the person being examined. The fan beams may be located in parallel planes, or the planes in which the fan beams are located may be angled relative to each other (e.g., by several degrees, up to 10-20 degrees). The X-ray module has at least two vertical columns and a mobile platform located between these columns for placing the person being examined.

The columns are located along the vertical axis of the body of the van, while the platform moves in a horizontal plane across the floor or the body of the van. A first detector of the X-ray radiation is located along the entire length of the first column, and optionally in a horizontal section of the overhead frame. One of the slit collimators is integrated in the second column. The collimator is rigidly connected to the source of radiation located on a special platform located near the outer surface of the second column.

One of the X-ray sources can move along a vertical axis using a hydraulic mechanism, or can rotate, so as to aim the fan-shaped X-ray beam at different portions of the body. Note that the beam needs to remain on the detector as the X-ray source moves or rotates. The second X-ray source's fan beam lowermost edge is aimed 2-5 degrees downward from the horizontal in order to scan a person's shoes.

In the mobile embodiment, horizontal rails are implemented on the floor of the van for allowing the person carrying platform to move across between the vertical columns. According to an exemplary embodiment, the platform can move from one side door of the van to the opposite side door. The X-ray module is separated from the driver area by at least one X-ray protective screen.

Figure 1A:
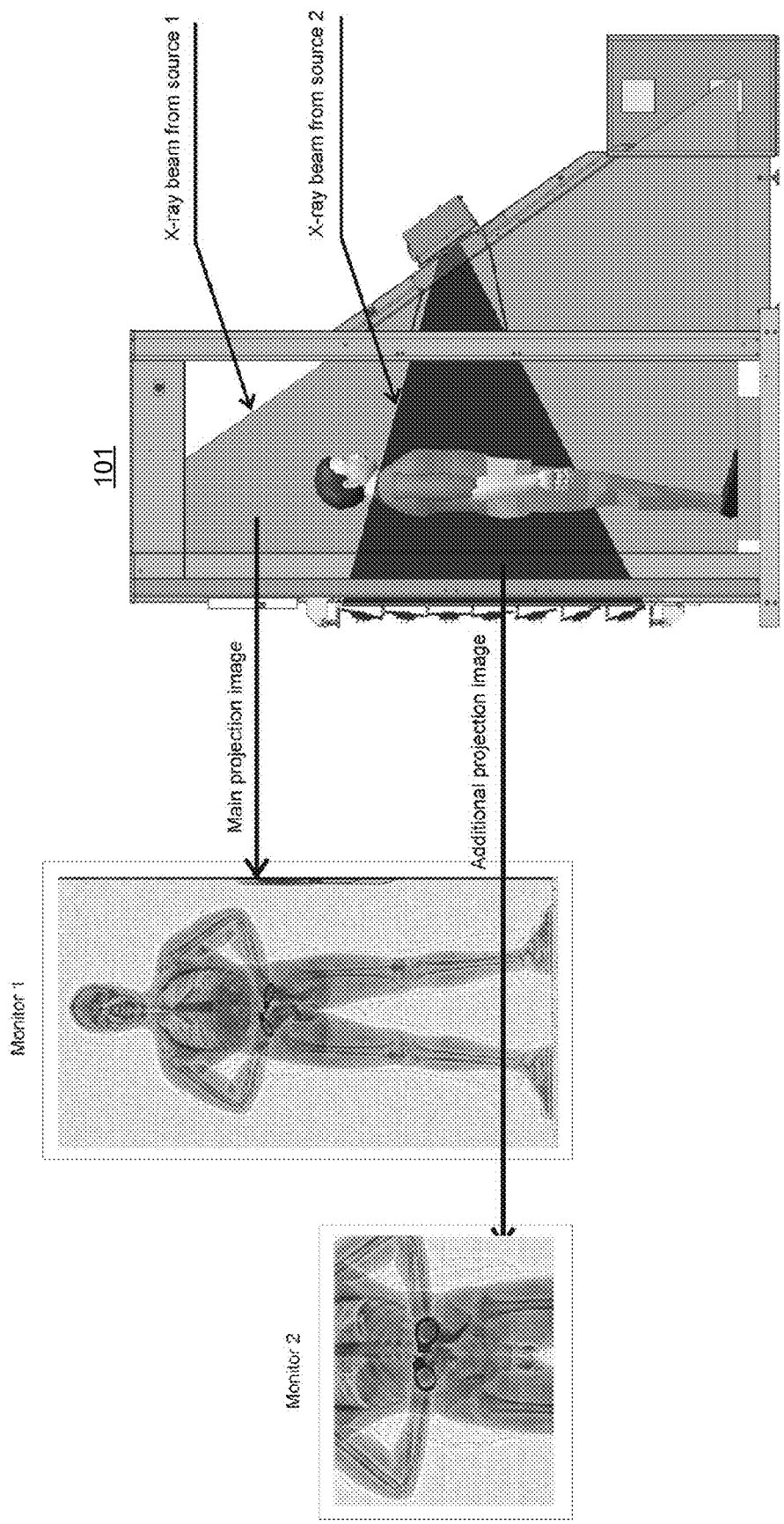
FIGS. 1A-1C illustrate the exemplary X-ray scanning system.
Figure 1B:
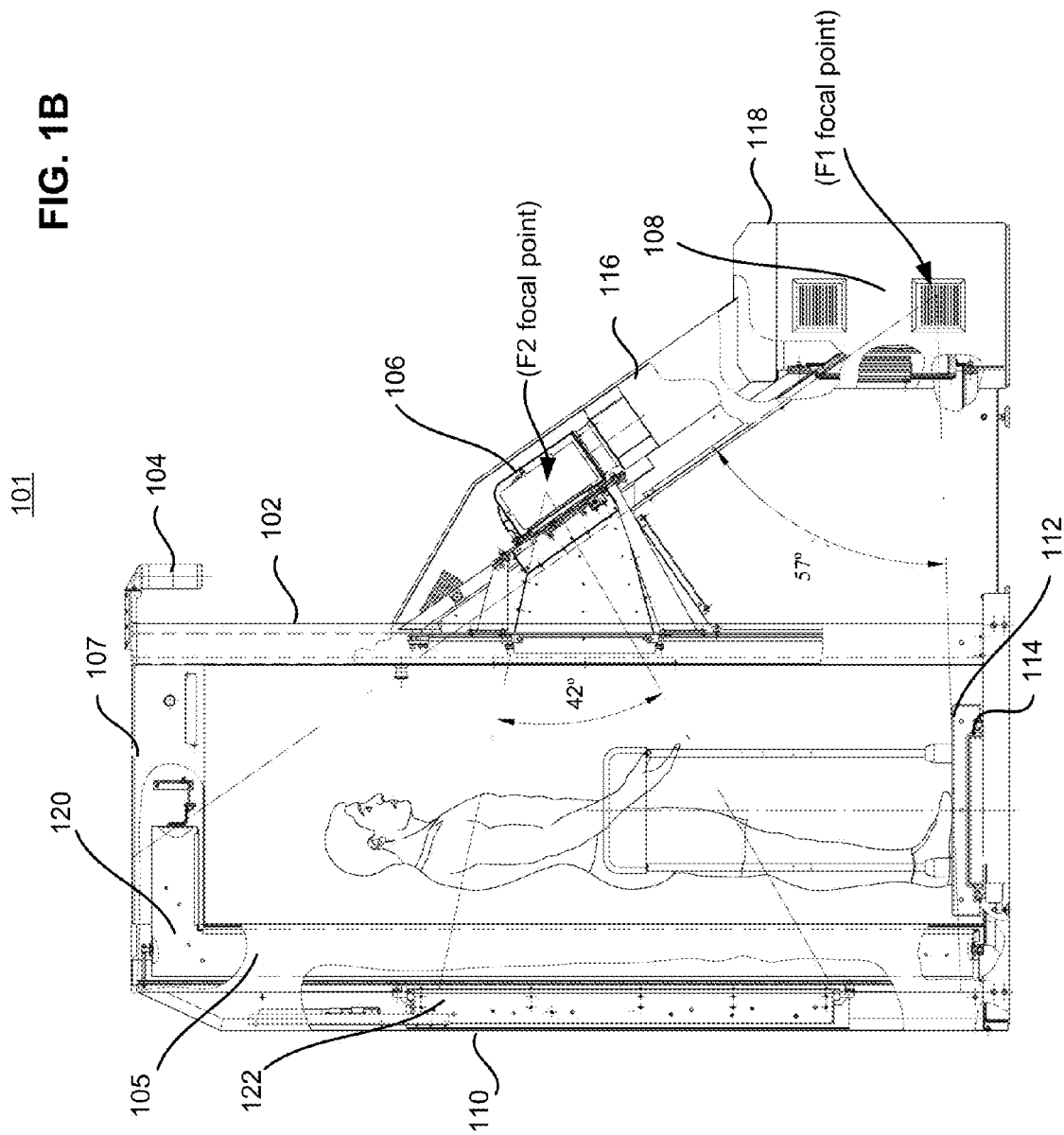
Figure 1C:
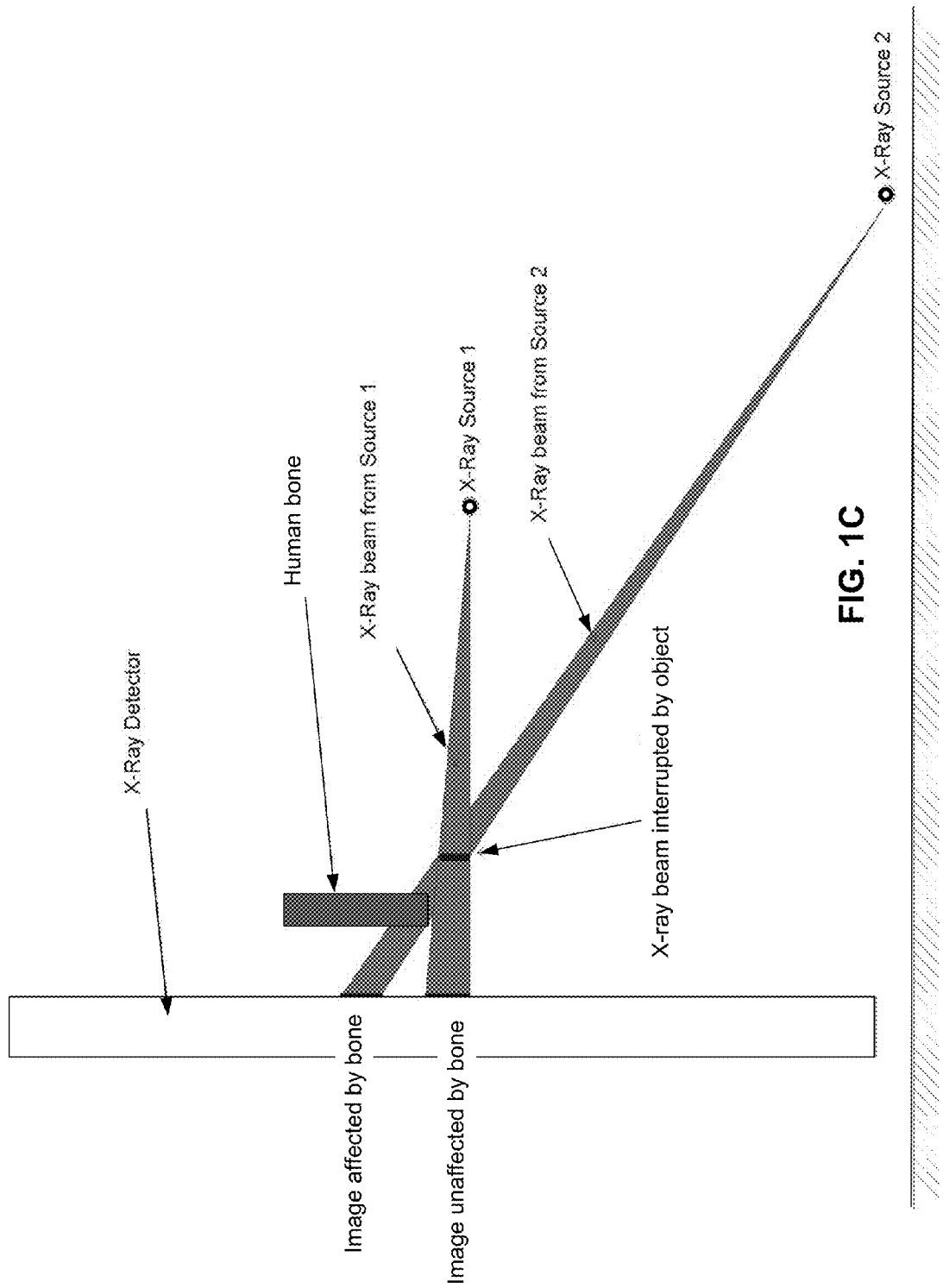

FIGS. 1A-1C illustrate the exemplary X-ray scanner 101 in more detail. Two vertical columns 102 and 105 are either standalone or attached to the floor of the van 1200 (see FIG. 12) along the longitudinal axis of the body of the van. A platform 114 moves in a horizontal plane across the floor or the body of the van. A linear detector of the X-ray radiation 122 is located along the entire length of one of the column 105 and covered by the housing 110. Another L-shaped linear detector 120 is located at the top upper corner adjacent to the column 105 and extending along the entire height of the scanner. A slit collimator is integrated in the second column 105 and covered by the housing 116. The collimator is rigidly connected to the sources of radiation 106 and 108.

The source of the radiation 106 is located on a special platform that can move along a vertical axis in order to scan the upper body of a person. The second column 105 has rails for vertical movement of the slit collimator 122. The second source of radiation 118 is located on a platform at floor level and can scan the lower body of a person.

The platform with the source of the radiation 118 creates a horizontal plane passing through the bottom of the person's body dissects 2-5 degrees from the radiation rays. The radiation source 106 platform can be moved in a vertical plane by a hydraulic lift in order to accommodate people of different sizes. Alternatively, angular positioning of the radiation source 106 can be changed.

A movable platform 112 for supporting a person being examined moves across the floor or across the body of the van 1200 along rails 114. The platform 112 has an integrated motor. The columns 105 and 102 are connected by a top bar 107 equipped with a signaling light 104, which indicates that the X-ray radiation is on. Both of the X-ray sources 106 and 118 can turn on simultaneously so the person's body is scanned in a single cycle from the head to the bottoms of the shoes and pseudo-stereoscopic images are generated. Alternatively, the broader (whole body) scan from X-ray source 108 can be performed first, and then a scan of the person's midsection using X-ray source 106 can be performed if necessary.

A person subject to examination enters the van from a side door and step onto the platform 114 powered by an electric motor. The platform 112 moves between the columns 102 and 105 on rails 114. Thus, the person' body crosses the X-rays coming from the X-ray sources 106 and 118. The X-rays passing through the body of the person at any moment are received by linear detectors 120 and 122 that convert received X-ray signal into digital signals. Not that the detector 120 consists of two linear detectors. In one embodiment, multi-energy detectors can be used for better recognition of the hidden objects. For example, a detector can process signals of 160 KV, 120 KV, 80 KV and 60 KV. This allows to recognize objects of organic nature (e.g., narcotics) hidden in the human body. The organic substance (such as narcotics) has an atomic mass similar to the human body, and signals of different energy produce better X-ray images, allowing for precise recognition of the organic objects inside a human body or hidden under clothing.

Figure 12:
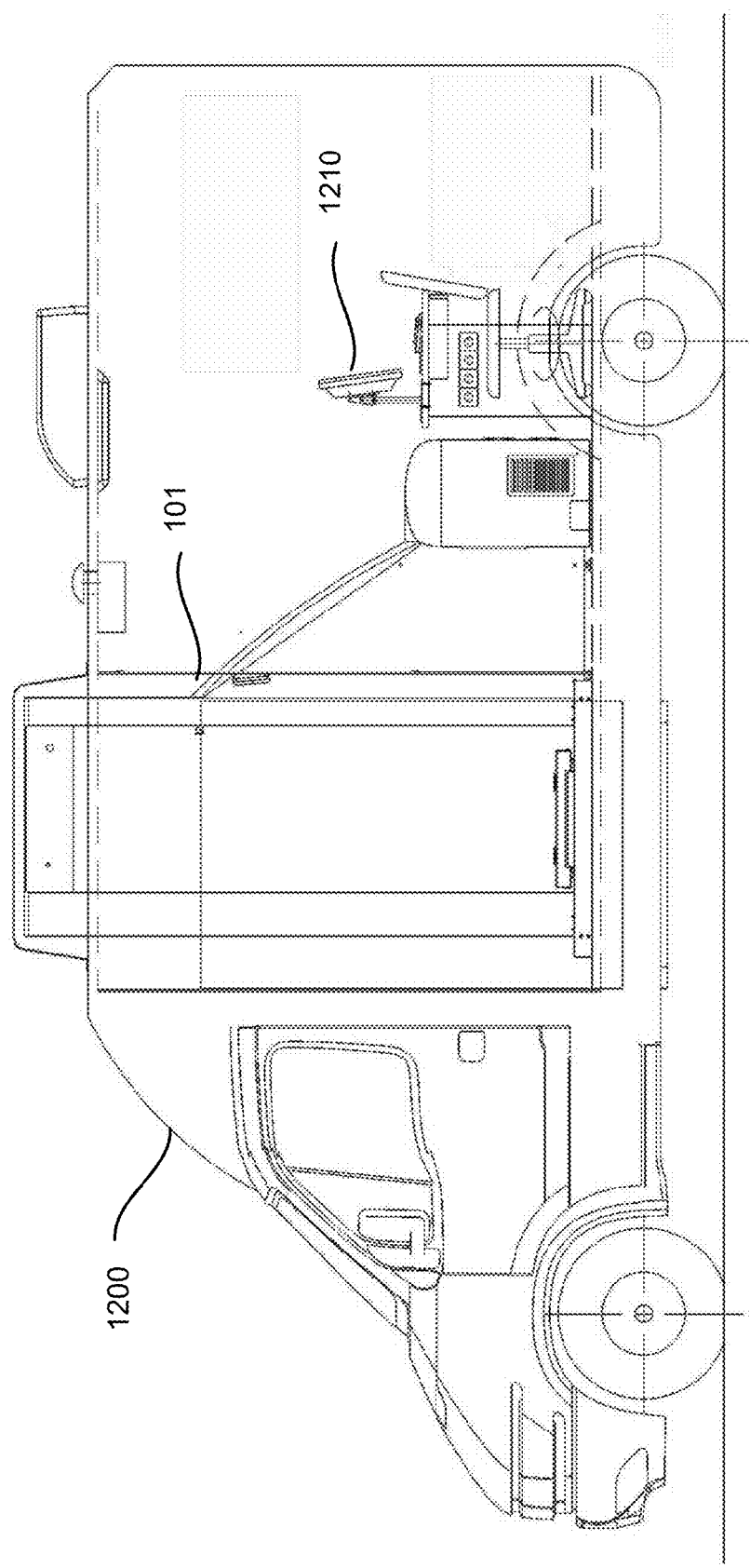
FIG. 12 illustrates an exemplary mobile X-ray device, in accordance with the exemplary embodiment.

The digital signals are passed on to operator work station 1210 (see FIG. 12). Then, the person steps off the platform 114 and exits the van through another side door. The X-ray sources 106 and 118 have focal points F1 and F2 respectively. The two focal areas, advantageously, provide for scanning of the entire body of the person in a latitudinal plane so any objects located inside the body are detected and not screened by the bones as may happened in case of scan with only one X-ray source. Note that the X-ray source 106 can be moved inside the housing 116 in order to get a more detailed view of a suspected area (e.g., chest or abdominal area). The exemplary embodiment produces a very low dose of radiation in any mode of operation. This allows for safe scanning of passengers, customers or spectators. The X-ray sources are placed into protective housing 108 and 116 respectively.

Note that the X-ray source 108 is less powerful (in unlimited range of radiation up to 0.25 microSieverts) than the source 106. In one embodiment, only the unlimited X-ray source 108 is used for most of the people being examined and the second more powerful (limited range of radiation—normally up to 2 microSieverts, with up to 10 microSieverts as permitted under ANSI standards) X-ray source 106 is used in case of suspicion that the person is hiding something inside his body. The X-ray sources may be operated simultaneously, or in sequence (e.g., source 106 first, then source 108, or vice versa), as selected by the operator.

Figure 2:
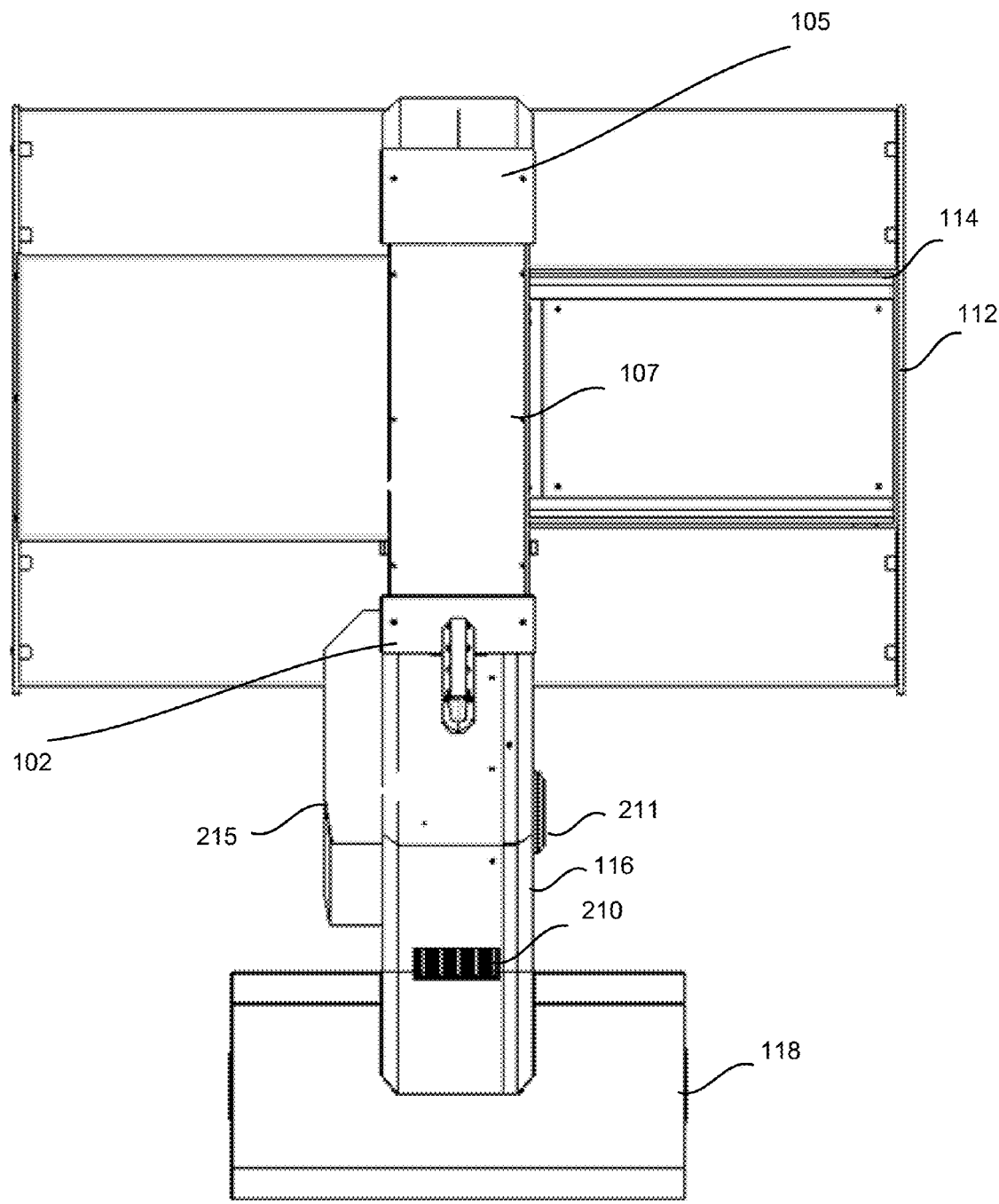
FIG. 2 illustrates a top view of the X-ray system, in accordance with the exemplary embodiment.

FIG. 2 illustrates a top view of the X-ray scanning system 101, in accordance with the exemplary embodiment. Units 211 and 210 represent ventilation covers mounted into the housing 116. An optional motor or a hydraulic mechanism for moving or rotating the radiation source 106 is located in housing 215. The radiation source can be repositioned or rotated to accommodate people of different sizes or heights.

Figure 3:
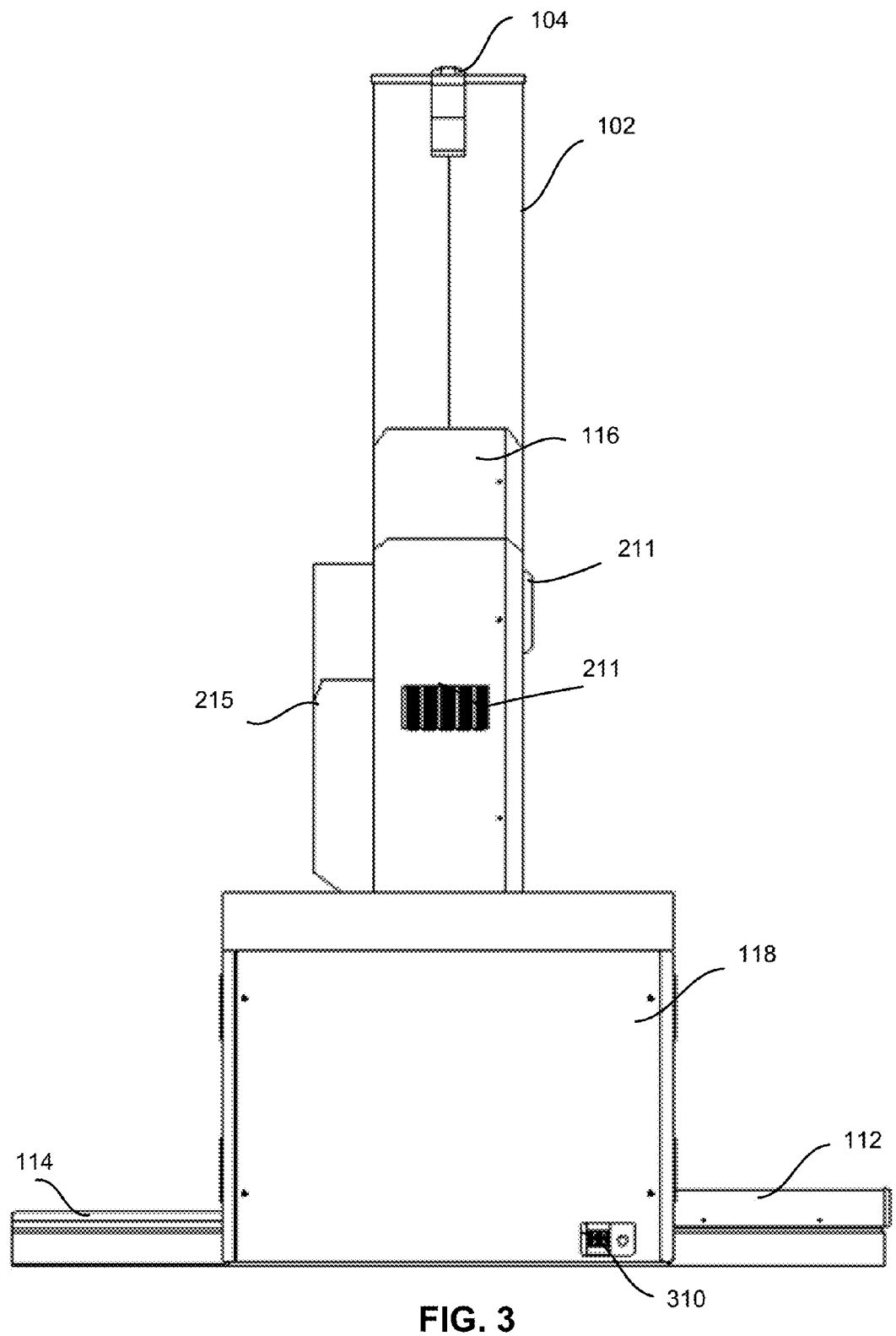
FIG. 3 illustrates a side view of the X-ray system.
Figure 4:
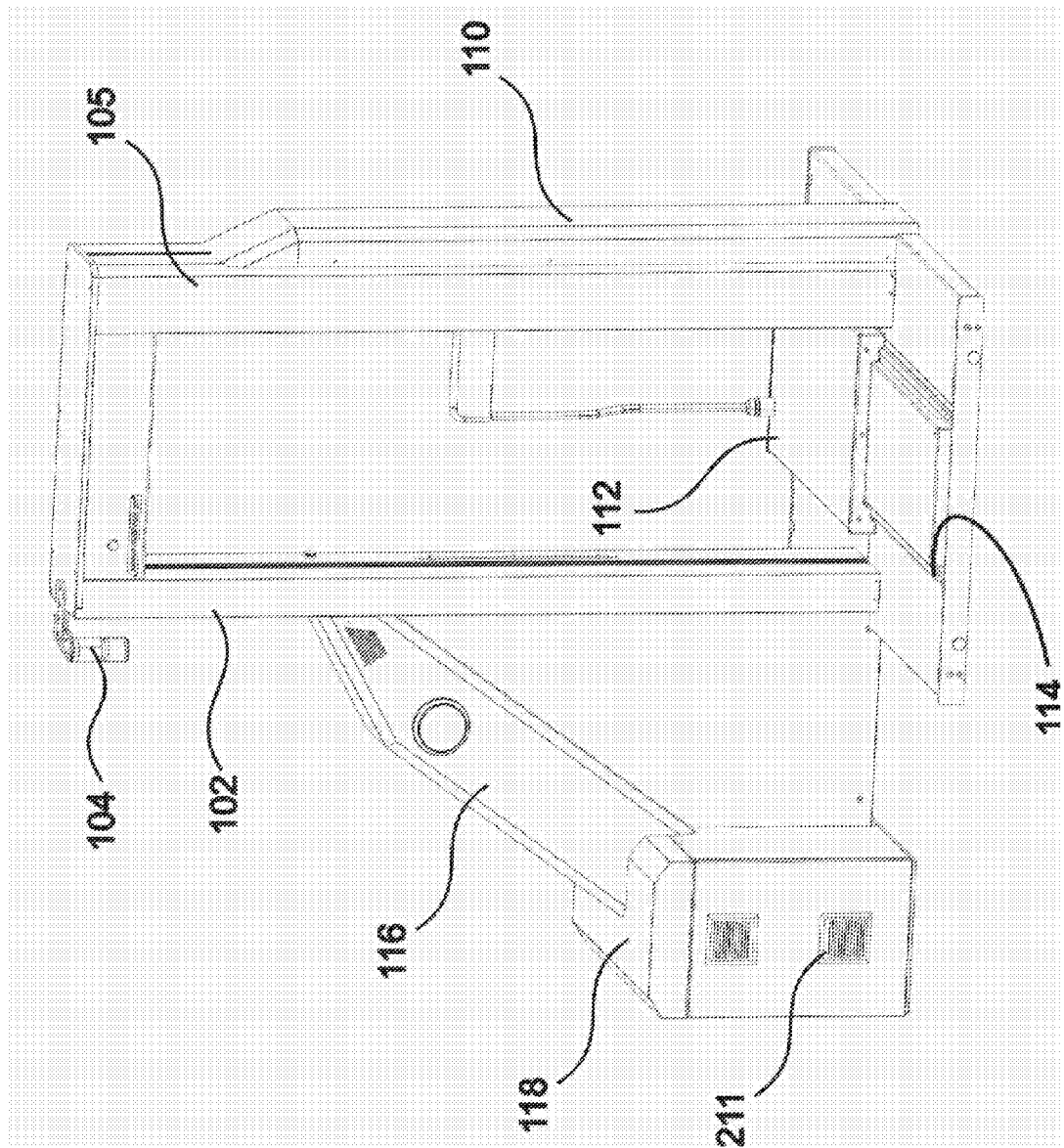
FIGS. 4-5 illustrate a system assembly shown from different angles.
Figure 5:
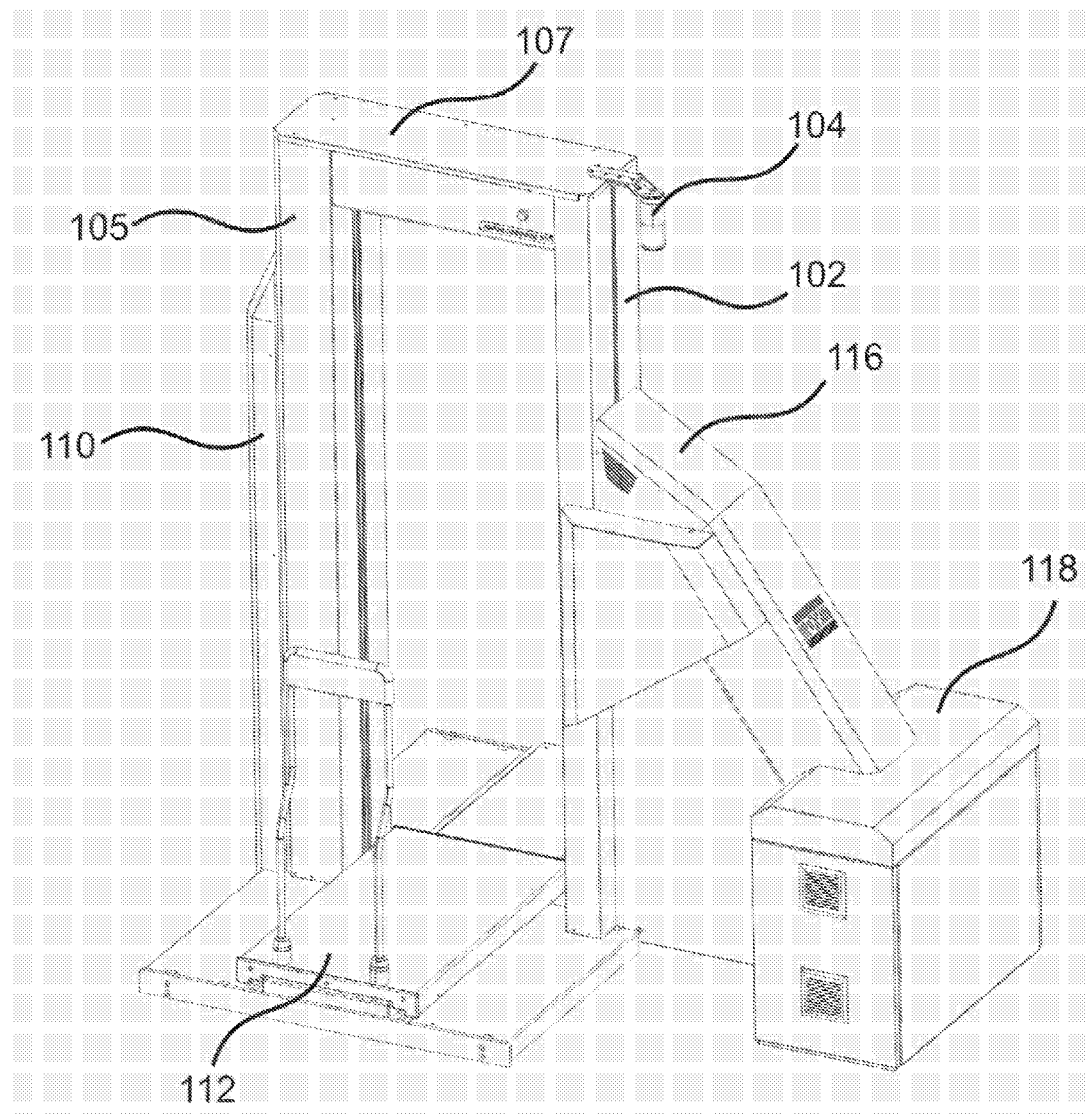

FIG. 3 illustrates a side view. Element 310 is a power outlet used for powering the X-ray scanning system 101. FIGS. 4-5 illustrate a system assembly shown from different angles.

Figure 6:
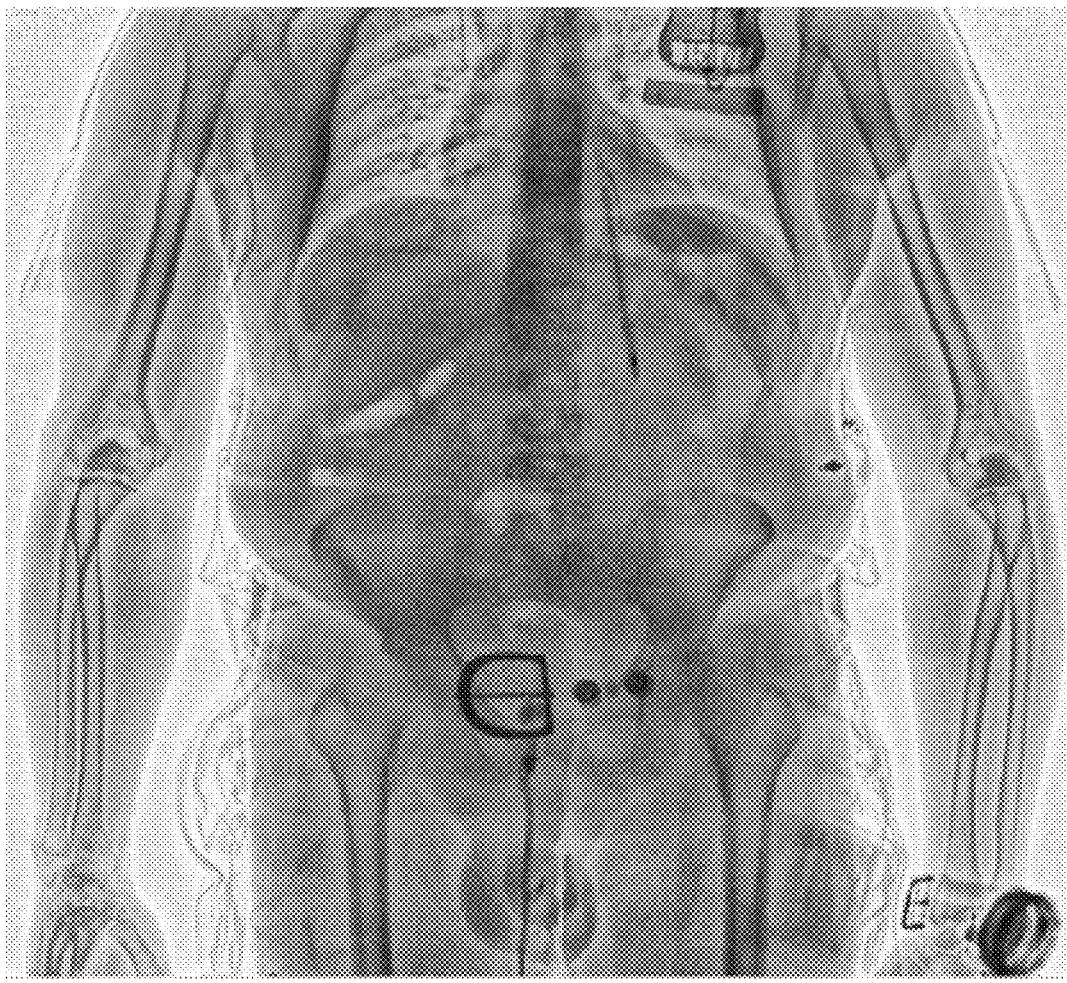
Figure 7:
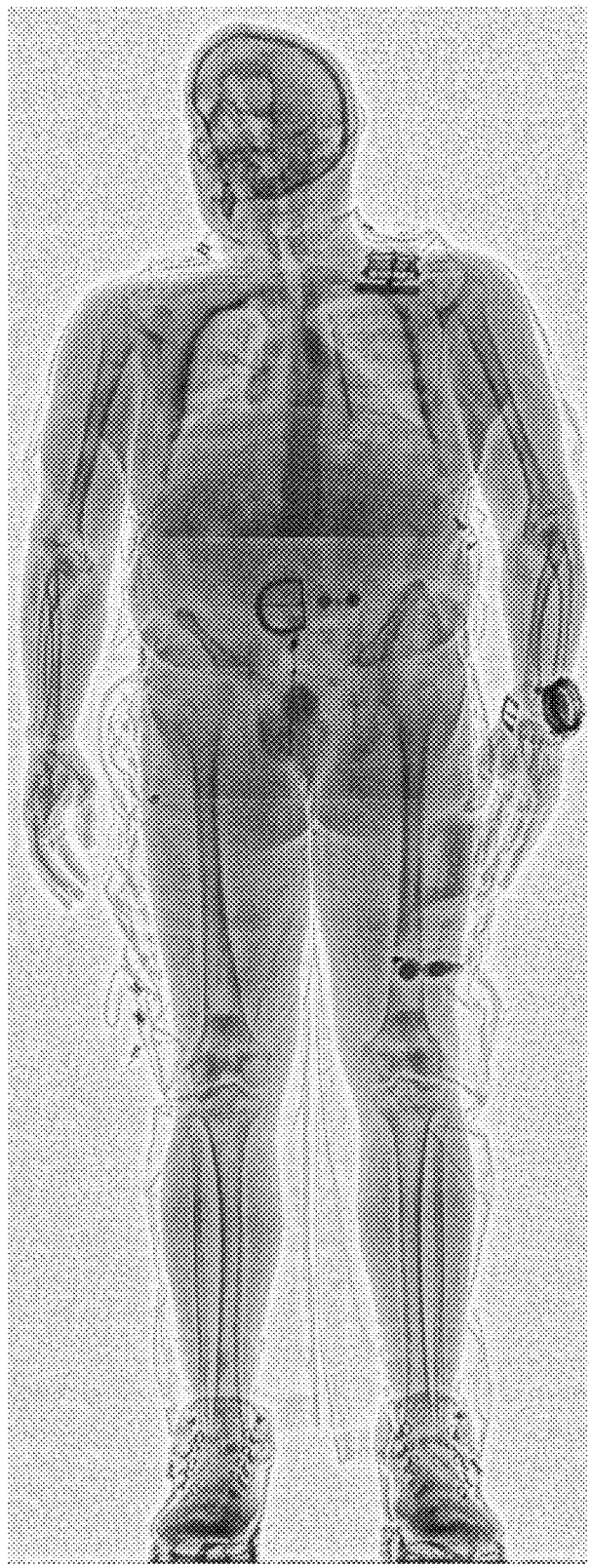
Figure 9:
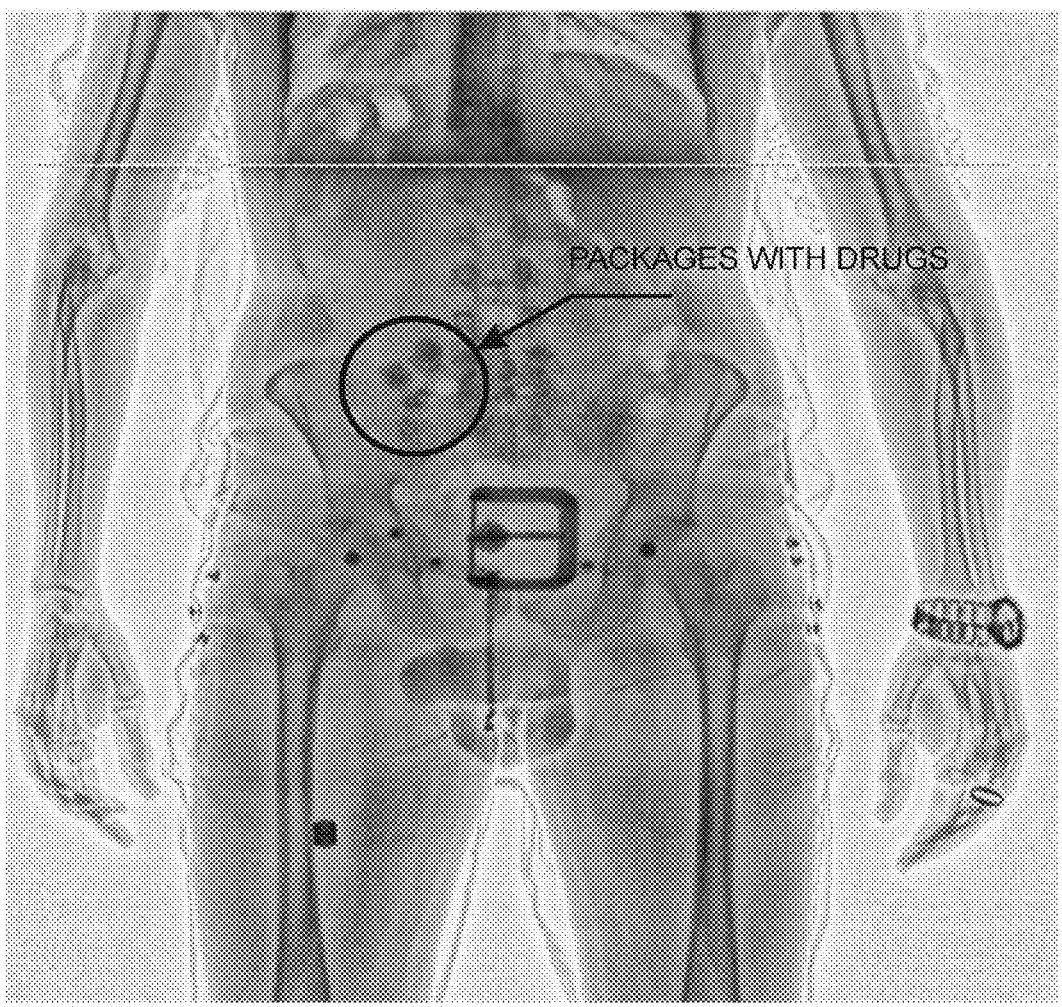
Figure 10:
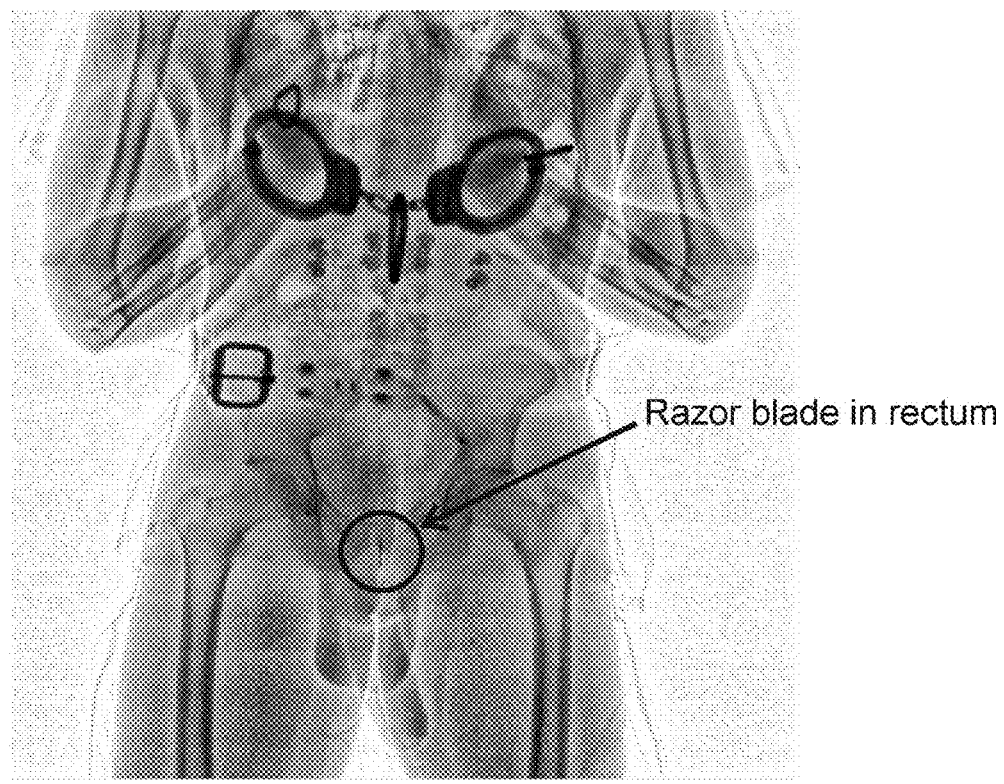

FIG. 6 illustrates an image produced by the high-intensity X-ray source depicting a razor blade hidden inside the body. FIG. 7 illustrates an image produced by the low-intensity X-rays source. This image indicates presence of a foreign object inside the body, but does not show the actual razor blade. FIG. 8 illustrates zoomed images showing the razor blade hidden inside person's colon. FIGS. 9 and 10 illustrate images of drugs hidden inside person's stomach. FIG. 11 illustrates zoomed-in images showing the hidden drugs (see circled areas).

An exemplary mobile X-ray scanning system is depicted in FIG. 12. The X-ray scanning system 101 is positioned inside the body of a van 1200. A module for processing and visualization of digital signals (not shown), operator work place 1210 and the X-ray scanning system 101 are located in a back of the van 1200 as shown in FIG. 13 depicting a top view of the van 1200.

Figure 13:
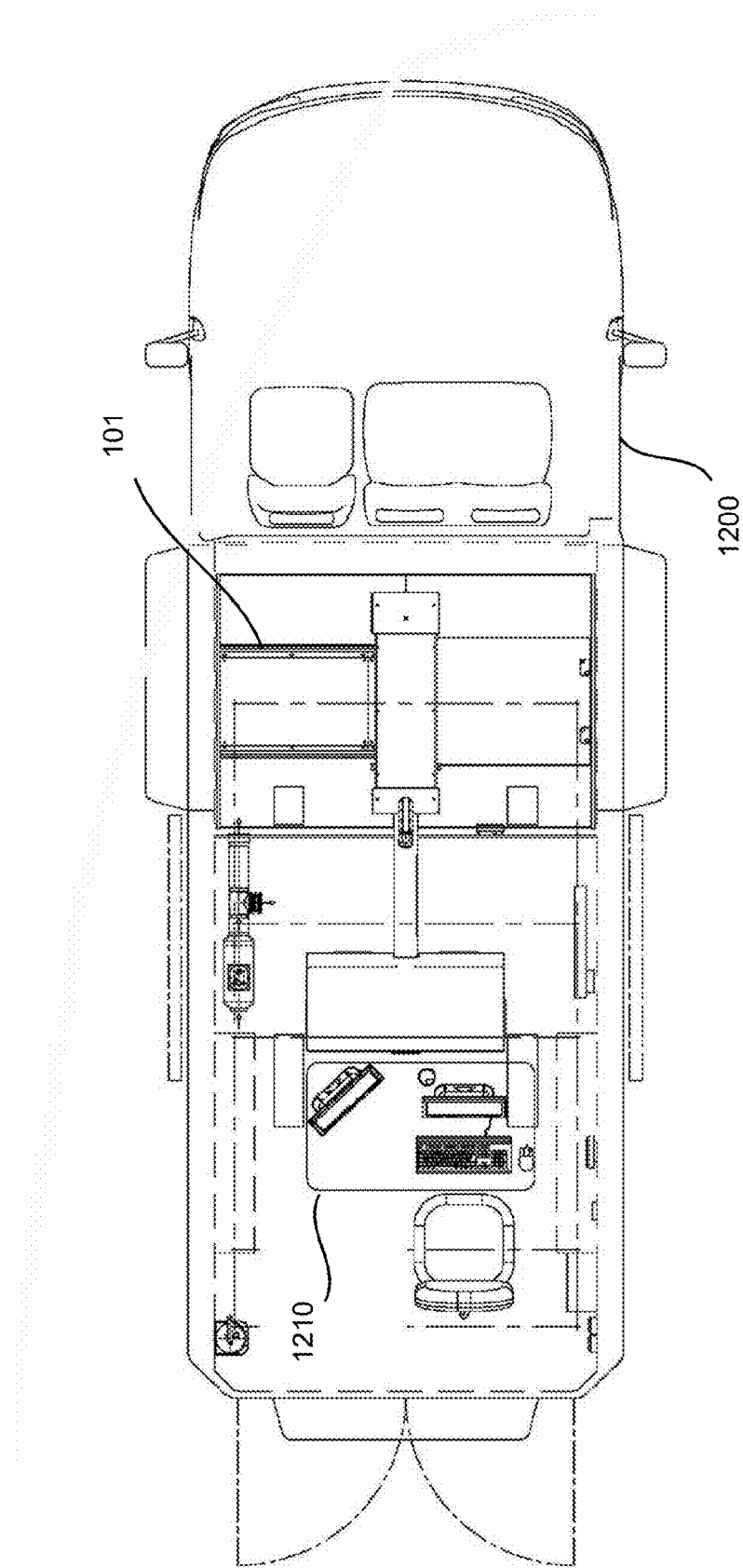
FIG. 13 illustrates a top view of the mobile X-ray system.

FIG. 13 illustrates a back view of the X-ray system 101, which may be stationary or located inside the van 1200 (see FIG. 12).

Figure 14:
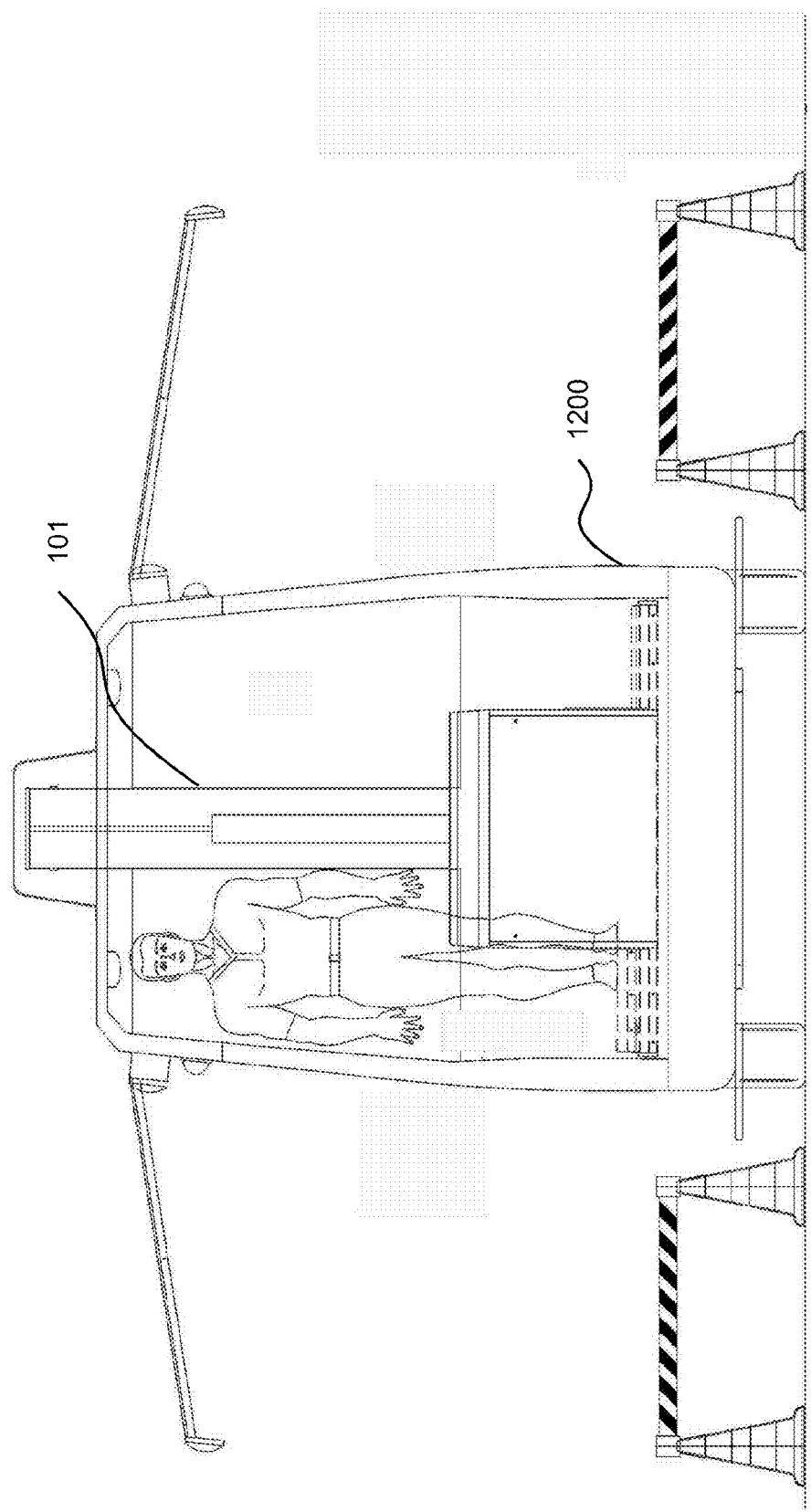
FIG. 14 illustrates a back view of the X-ray system located inside a van.

FIG. 14 illustrates a top view of the mobile X-ray system 101.

Having thus described a preferred embodiment, it should be apparent to those skilled in the art that certain advantages of the described method and apparatus have been achieved.

It should also be appreciated that various modifications, adaptations, and alternative embodiments thereof may be made within the scope and spirit of the present invention. The invention is further defined by the following claims.

What is claimed is:

1. An X-ray examination station comprising:
    a first source of X-ray radiation for whole body scanning and positioned at ground level;
    a first collimator for forming a first fan beam of X-ray radiation from the first source;
    a first radiation detector configured to detect the first fan beam transmitted through a human body;
    a second source of X-ray radiation installed at mid-height of a person being examined, on the same side of the person as the first source, for scanning a central torso portion of the human body below the head and above the knee;
    a second collimator for forming a second fan beam of X-ray radiation from the second source of X-ray radiation; and
    a second detector of X-ray radiation configured to detect the second fan beam transmitted through the human body,
    wherein the first and the second radiation fan beams are emitted in parallel planes,
    wherein the first X-ray radiation source is turned on for the whole body scanning; and
    wherein the second X-ray radiation source is turned on for scanning the torso portion.

2. The system of claim 1, wherein the first source and the second source are turned on simultaneously to form pseudo-stereoscopic images.

3. The system of claim 1, wherein the first source and the second source are turned on sequentially to form pseudo-stereoscopic images.

4. The system of claim 1, wherein the first detector is positioned along an entire vertical height of the X-ray scanner to detect the first fan beam.

5. The system of claim 1, further comprising a horizontal linear detector located in an upper portion of a housing the X-ray scanner, such that the first detector and the horizontal linear detector together form an "U'.

6. The system of claim 1, wherein the second detector is approximately 36inches long.

7. The system of claim 1, wherein the second source is movable vertically.

8. The system of claim 1, wherein the second X-ray source is rotatable about its axis.

9. The system of claim 1, further comprising a control unit configured to turn on the first and second sources.

10. A mobile X-ray system comprising:
    an X-ray scanner, including a digital imaging module, located inside a cargo area of a motor vehicle;
    a module for visualization of digital signals from the digital imaging module;
    the X-ray scanner further including:
        a first source of X-ray radiation for whole body scanning and positioned at ground level;
        a first collimator for forming a first fan beam of X-ray radiation from the first source;
        a first radiation detector configured to detect the first fan beam transmitted through a human body;
        a second source of X-ray radiation installed at mid-height of a person being examined, for scanning a torso portion of the human body below the head and above the knee;
        a second collimator for forming a second fan beam of X-ray radiation from the second source of X-ray radiation; and a second detector of X-ray radiation configured to detect the second fan beam transmitted through the human body, wherein the first X-ray radiation source is turned on for the whole body scanning, and wherein the second X-ray radiation source is turned on for scanning the torso portion.

11. The system of claim 10, wherein the first and the second X-ray sources are turned on simultaneously in order to form pseudo-stereoscopic images.

12. The system of claim 10, wherein the first source and the second source are turned on simultaneously to form pseudo-stereoscopic images.

13. The system of claim 10, wherein first detector is positioned along an entire vertical height of the X-ray scanner to detect the first fan beam.

14. The system of claim 10, further comprising a horizontal linear detector located in an upper portion of a housing the X-ray scanner, such that the first detector and the horizontal linear detector together form an "L".

15. The system of claim 10, wherein the second source is rotatable about its axis.

16. The system of claim 10, further comprising a platform for laterally moving the human body being scanned.

17. The system of claim 10, wherein the first and the second radiation fan beams are emitted in parallel planes.

18. The system of claim 10, wherein the first and the second radiation fan beams are emitted in non-parallel planes that are at angle to each other of up to 20 degrees.

19. An X-ray examination station comprising:

a first source of X-ray radiation;

a first collimator for forming a first fan beam of X-ray radiation from the first source;

a first radiation detector aligned with the first fan beam for detecting the first fan beam transmitted through a human body;

a second source of X-ray radiation installed at mid-height of a person being examined, for scanning only a torso portion of the human body below the head and above the knee;

a second collimator for forming a second fan beam from the second source; and a second detector of X-ray radiation aligned with the second fan beam transmitted through the human body, wherein the first source is turned on for the whole body scanning, and wherein the second source is turned on only for scanning the torso portion.

* * * * *